(12) United States Patent
Pretsch et al.

(10) Patent No.: US 9,567,294 B2
(45) Date of Patent: Feb. 14, 2017

(54) BIOACTIVE POLYMERS

(71) Applicant: Sealife Pharma GmbH, Tulln (AT)

(72) Inventors: Alexander Pretsch, Gainbrunn (AT); Michael Nagl, Vienna (AT); Christoph Wiesner, Vienna (AT); Heinz Burgmann, Vienna (AT)

(73) Assignee: Sealife Pharma GmbH, Tulln (AT)

( * ) Notice: Subject to any disclaimer, the term of this patent is extended or adjusted under 35 U.S.C. 154(b) by 0 days.

(21) Appl. No.: 14/763,356

(22) PCT Filed: Jan. 22, 2014

(86) PCT No.: PCT/AT2014/050026
§ 371 (c)(1),
(2) Date: Jul. 24, 2015

(87) PCT Pub. No.: WO2014/113835
PCT Pub. Date: Jul. 31, 2014

(65) Prior Publication Data
US 2015/0368193 A1 Dec. 24, 2015

(30) Foreign Application Priority Data
Jan. 25, 2013 (AT) .................................. A 53/2013

(51) Int. Cl.
| C07C 279/00 | (2006.01) |
| C08G 73/02 | (2006.01) |
| A01N 47/40 | (2006.01) |
| C07C 277/08 | (2006.01) |
| C07C 279/08 | (2006.01) |

(52) U.S. Cl.
CPC ............ *C07C 279/00* (2013.01); *A01N 47/40* (2013.01); *C07C 277/08* (2013.01); *C07C 279/08* (2013.01); *C08G 73/02* (2013.01)

(58) Field of Classification Search
CPC ..... A01N 47/40; C07C 277/08; C07C 279/00; C07C 279/08
See application file for complete search history.

(56) References Cited

U.S. PATENT DOCUMENTS

| 2,325,586 A | 7/1943 | Bolton et al. | |
| 5,612,332 A * | 3/1997 | Wagle | A61K 8/43 514/211.01 |
| 2009/0130052 A1* | 5/2009 | Schmidt | A01N 47/44 424/78.37 |
| 2011/0269936 A1* | 11/2011 | Tets | A61K 31/155 528/422 |

FOREIGN PATENT DOCUMENTS

| AT | 411060 B | 9/2003 |
| CN | 103145981 A | 6/2013 |
| EP | 2520605 A1 | 11/2012 |
| GB | 1095902 A | 12/1967 |
| WO | 9954291 A1 | 10/1999 |
| WO | 0185676 A1 | 11/2001 |
| WO | 0230877 A1 | 4/2002 |
| WO | 2006047800 A1 | 5/2006 |
| WO | 2011043690 A1 | 4/2011 |

OTHER PUBLICATIONS

International Search Report issued Jun. 27, 2014 in International Application No. PCT/AT2014/050026.
Written Opinion issued Jun. 27, 2014 in International Application No. PCT/AT2014/050026.
Search Report issued Jul. 12, 2013 in AT Application No. A 53/2013.
Albert et al., "Structure-Activity Relationships of Oligoguanidines—Influence of Counterion, Diamine, and Average Molecular Weight on Biocidal Activities," Biomacromolecules, vol. 4, pp. 1811-1817 (2003).
Feiertag et al., "Structural characterisation of biocidal oligoguanidines," Macromolecular Rapid Communications, vol. 24, No. 9, pp. 567-570 (2003).

* cited by examiner

*Primary Examiner* — Timothy Thomas
*Assistant Examiner* — Andrew S Rosenthal
(74) *Attorney, Agent, or Firm* — Panitch Schwarze Belisario & Nadel LLP

(57) ABSTRACT

Polycondensation products of aminoguanidine and/or 1,3-diaminoguanidine with one or more diamines are provided including polyguanidine derivatives of the following formula (I) or a salt thereof:

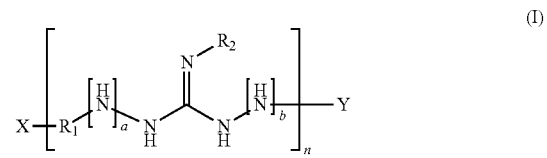

wherein X is selected from $-NH_2$, aminoguanidino and 1,3-diaminoguanidino; Y is selected from —H and $-R_1-NH_2$; or X and Y together represent a chemical bond to give a cyclic structure; $R_1$ is selected from divalent organic radicals having 2 to 20 carbon atoms, in which optionally one or more carbon atoms are replaced by O or N; a and b are each 0 or 1, wherein $a+b \neq 2$ if no 1,3-diaminoguanidine units are included; $R_2$ is selected from —H and $-NH_2$, wherein $R_2$ is $-NH_2$ if $a+b=0$, $R_2$ is —H or $-NH_2$ if $a+b=1$, and $R_2$ is —H if $a+b=2$; and $n \geq 2$. Production methods and uses of the polyguanidine derivatives are also provided.

19 Claims, 1 Drawing Sheet

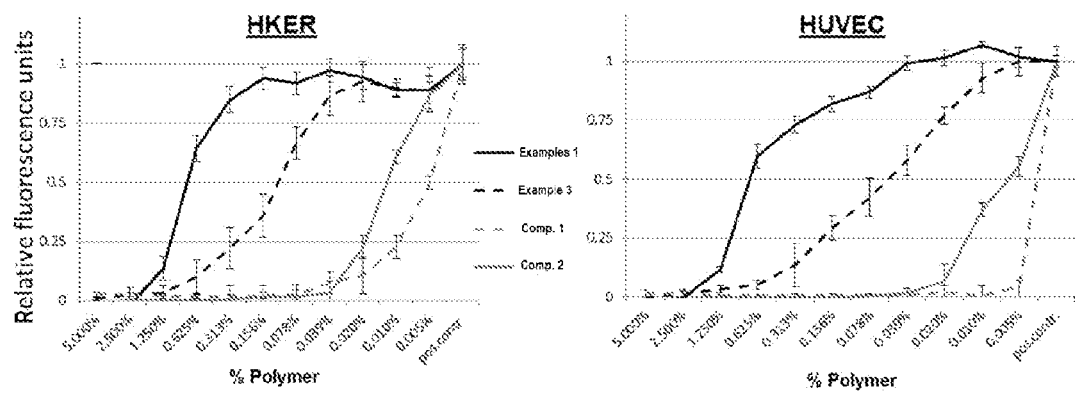

BIOACTIVE POLYMERS

CROSS-REFERENCE TO RELATED APPLICATION

This application is a Section 371 of International Application No. PCT/AT2014/050026, filed Jan. 22, 2014, which was published in the German language on Jul. 31, 2014, under International Publication No. WO 2014/113835 A1, and the disclosure of which is incorporated herein by reference.

The present invention relates to new bioactive polymers as well as their use as biocides.

STATE OF THE ART

Polyguanidines of the following general formula as well as various derivatives thereof have been known for a long time.

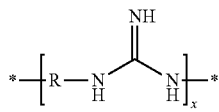

Already in 1943, patent literature described in U.S. Pat. No. 2,325,586 several methods for producing various polyguanidines by polycondensation of i) guanidine or salts thereof, ii) cyanohalides, iii) dicyanoamides, or iv) isocyanide dihalides with diamines, or of v) two dicyanodiamides together (which results in cyano-substituted polyguanidines), as well as the use of polyguanidines thus produced as dyeing aids:

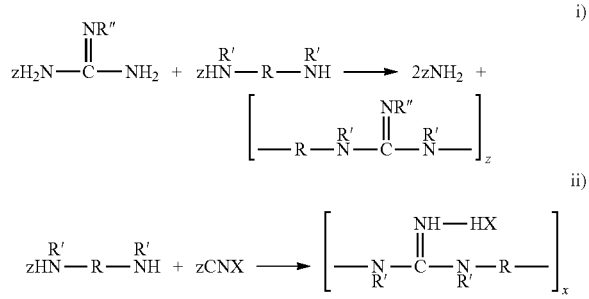

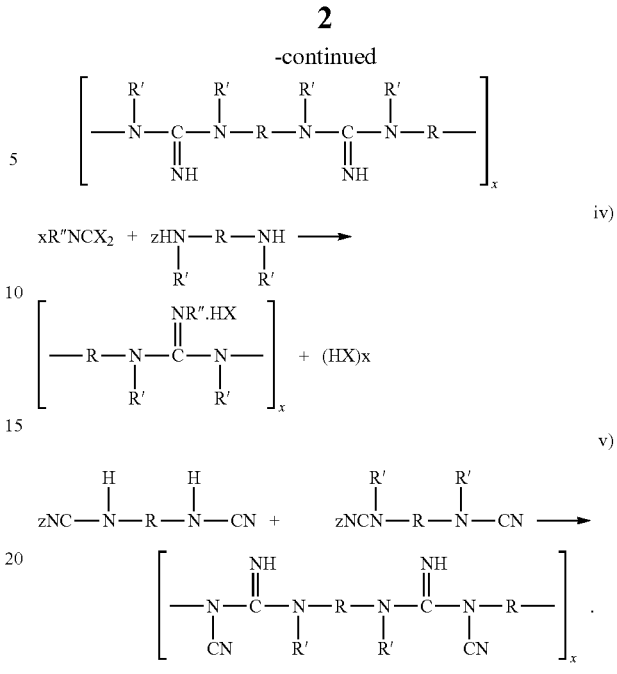

Already at that time, the diamines in the reactions i) to iv) disclosed were alkylene and phenylene diamines as well as oxyalkylene or other polyether diamines, which later also became known as Jeffamines®.

Decades later, such polyguanidines have proven to be excellent biocides. A group around Oskar Schmidt discloses in WO 99/54291 A1 the production of microbiocidal poly(hexamethylene guanidines), in WO 01/85676 A1 biocidal polyguanidines that are produced by condensation of guanidine with polyoxyalkylenes, and in WO 2006/047800 A1 polyguanidine derivatives acting as biocides, in particular as fungicides, which are produced by polycondensation of guanidine with a mixture of alkylene diamine and oxyalkylene diamine and are said to possess lower toxicity than polymers containing only one of the two types of the divalent radical $R_1$.

WO 02/30877 A1 describes similar polyguanidines used as disinfectants, which additionally contain phenylene moieties in the chains. A Russian group of researchers (Tets, Tets and Krasnov) discloses in WO 2011/043690 A1, from which US 2011/0269936 A1 and EP 2,520,605 A1 were derived, biocidal polyguanidines of the following formula, which are produced by polycondensation of guanidine and hexamethylene diamine in the presence of hydrazine hydrate:

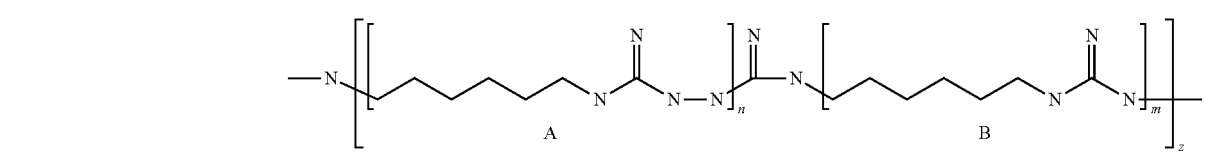

Thus, during polycondensation, the hydrazine replaces—at least formally—an amino group of only one guanidine moiety or also of two guanidine moieties, which is said to result in block copolymers with alternating poly(hexamethylene guanidine) blocks and poly(hexamethylene aminoguanidine) blocks, wherein the two types of blocks are linked via guanidine dimers, as shown below:

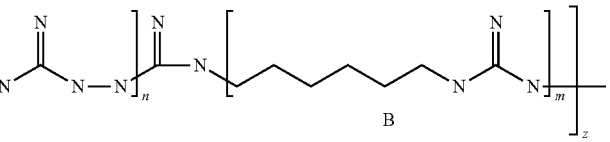

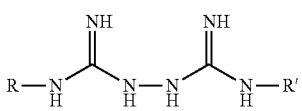

These polymers and acid addition salts thereof are also said to act as biocides against bacteria, viruses, and fungi. However, the examples given in this application, in which 7 different polymers were produced, do not contain any physical data on the products obtained except for the statement that the polymer of Example 1 is a "solid, almost colorless, transparent substance."

Regarding the possible structures that may form during polycondensation of guanidines with diamines, there are several articles by a group of researchers from Graz University of Technology, e.g. Albert et al., Biomacromolecules 4(6), 1811-1817 (2003), and Feiertag et al., Macromol. Rap. Comm. 24(9), 567-570 (2003). In addition to the different possibilities of terminating the linear polymer chains with one of the starting monomers, usually cyclic molecules of the following general formula are also formed at a portion not to be neglected, which, among other things, depends on the chain length of the diamine:

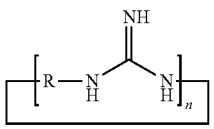

The main disadvantages of practically all polyguanidine derivatives described above is, on the one hand, the toxicity of these products that is not to be neglected as well as—in case highly reactive components are used—their comparatively laborious production methods, in addition to the use of, as is known from the toxicological field, problematic components such as hydrazine, which is why the object of the invention was the production of new, less toxic, but still biocidally effective polyguanidines in a fashion as simple and economic as possible and avoiding the above disadvantages.

DISCLOSURE OF THE INVENTION

The present invention achieves this object by providing new polycondensation products of aminoguanidine and/or 1,3-diaminoguanidine with one or more diamines, i.e. of polyguanidine derivatives of the following formula (I):

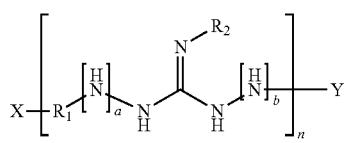

wherein
X is selected from —NH$_2$, aminoguanidino, and 1,3-diaminoguanidino;
Y is selected from —H and —R$_1$—NH$_2$;
or X and Y together represent a chemical bond to give a cyclic structure;
R$_1$ is selected from divalent organic radicals having 2 to 20 carbon atoms, in which optionally one or more carbon atoms are replaced by O or N;
a and b are each 0 or 1,
wherein a+b≠2 if no 1,3-diaminoguanidine units are contained;
R$_2$ is selected from —H and —NH$_2$,
wherein R$_2$ is —NH$_2$ if a+b=0,
R$_2$ is —H or —NH$_2$ if a+b=1, and
R$_2$ is —H if a+b=2; and
n≥2;
or of salts thereof.

In activity assays, the new polyguanidine derivatives of formula (I) have proven to be effective antimicrobial substances, which, however, surprisingly show much lower toxicity than the structurally similar polymers of the above documents WO 2011/043690 A1, US 2011/0269936 A1 and EP 2,520,605 A1, as will be substantiated by embodiments of the invention and comparative examples below. Without wishing to be bound by any theory, the inventors assume that amino- and diaminoguanidino moieties are better tolerated by human eukaryotic cells that guanidino moieties and in particular than the polymers containing the hydrazo-bridged guanidine dimers shown above. In addition, the method disclosed avoids the use of the toxic component, hydrazine hydrate, in the polymerization process, which may be contained as a residual monomer in some polymers according to the state of the art.

The above formula (I) refers to polycondensation products of (mono)aminoguanidine, in the following referred to as MAG, as well as of 1,3-diaminoguanidine, in the following referred to as DAG.

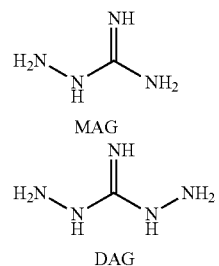

Formula (I) may be explained by the fact that during polycondensation proceeding with concomitant separation of ammonia, MAG and DAG radicals can take part in this polycodensation via their amino or tautomeric imino groups as well as their hydrazo (hydrazinyl) moieties. Consequently, there are three different possibilities for MAG and DAG as starting monomers to be integrated into the chains of the inventive polymers. In the case of MAG, the only hydrazo moiety in formula (I), in the case of DAG the only imino/amino moiety, can point to the left, to the right or upwards.

For MAG, this means the following possible parameter in formula (I):
a=1, b=0, R$_2$ is —H: hydrazo moiety points to the left;
a=0, b=1, R$_2$ is —H: hydrazo moiety points to the right; or
a=0, b=0, R$_2$ is —NH$_2$: hydrazo moiety points upwards.

For DAG, there are the following parameter combinations:
a=0, b=1, R$_2$ is —NH$_2$: amino/imino moiety points to the left;

a=1, b=0, R$_2$ is —NH$_2$: amino/imino moiety points to the right; or a=1, b=1, R$_2$ is —H: amino/imino moiety points upwards.

Without being limited thereto, NMR spectra of the polycondensates obtained seem, as will be described in later examples of the invention, to prove that the polycondensation reactions consistently result in mixtures of several of the three possible orientations, which leads to the presumption that several orientations of one and the same monomer are present within a chain (which has not been clarified 100% yet).

In this connection, it should be explicitly mentioned that the position of C═N double bonds of guanidino moieties—as well as the spatial position of substituent R$_2$ at the double bond—is subject to the usual effects of tautomerism. This means that the double bond of guanidine may be within or outside the chain and that R$_2$ may point to the left or to the right. Such tautomers of the above polycondensation products of formula (I) are thus also within the scope of the present invention.

The above options for X and Y result from the different possibilities of terminating chains—depending on whether MAG, DAG, or a mixture of both was used as starting monomer(s)—including the possibility of a cyclization to obtain a cyclic polycondensate. See also the articles mentioned above by Albert et al. and by Feiertag et al. Of course, the same options are available for terminal aminoguanidino (MAG) and 1,3-diaminoguanidino (DAG) moieties as for moieties within a chain, i.e. the attachment to the chain may be via any nitrogen atom.

According to the present invention, the radical R$_1$ may be a linear, branched or cyclic, saturated or unsaturated, divalent hydrocarbon radical having 2 to 20 carbon atoms, preferably 4 to 18 carbon atoms, more preferably 6 to 12 carbon atoms, in which some C atoms may be replaced by O and/or N. The above preferences are the result of the following considerations. In the case of very short radicals R$_1$, the active MAG or DAG moieties are very close to each other, which may reduce the activity of the polymers; with longer radicals, however, they are quite far apart. Radicals having more than 20 atoms are thus basically possible, however, they are not preferred from the economic point of view because they result in polymers of formula (I) in which relatively few antiinfectively effective guanidino moieties are contained per weight unit.

Preferably, the radical R$_1$ is selected from alkylene radicals in which optionally one or more carbon atoms are replaced by O or N to increase the hydrophilicity of the chain, more preferably R$_1$ is selected from radicals of the following general formulas (II) to (V):

(II)

(III)

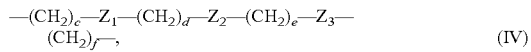
(IV)

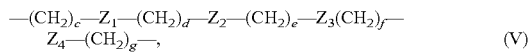
(V)

wherein Z$_1$ to Z$_4$ are each independently a heteroatom selected from O and N, and the indexes c to g are each independently integers in the range of 1 to 12, so that the total number of atoms of radical R$_1$ does not exceed 20. Especially preferred is that all heteroatoms Z within one radical R$_1$ are either O or N.

The best results in assays on biocidal effect or toxicity were achieved with compounds in which R$_1$ represents the divalent radical of a polyether diamine such as 4,9-dioxadodecane-1,12-diamine, a polyoxyethylene and/or propylene diamine, wherein n is preferably 2 to 15, more preferably 2 to 10, most preferably 2 to 6.

Useful salts of the new polyguanidines of formula (I) are any acid addition salts with one or more inorganic or organic acids, such as hydrohalic acids, oxygen acids of nitrogen, sulphur or phosphor, boric acid, carbonic acid, carboxylic, thiocarboxylic, carbamic, sulfonic, phosphonic or phosphinic acids, as well as partial esters or amides of multivalent forms of these acids. According to the invention, pharmaceutically acceptable salts are preferably used, more preferably acid addition salts in the form of a hydrogen chloride, hydrogen bromide, hydrogen iodide, sulfate, methylsulfate, carbonate, borate, cyanate, thiocyanate, phosphate, mesylate, nitrate, acetate, benzoate, lactate, tartrate, citrate, maleate, fumarate or partial esters of these acids in case they are difunctional or higher. A preferred alcoholic component of such partial esters is a pharmaceutically acceptable alcohol, in particular ethanol.

If the radical R$_1$ contains one or more OH or COOH groups, salts with inorganic or organic bases are also within the scope of the present invention, preferably with pharmaceutically acceptable bases, more preferably with a guanidine derivative, in particular with amino or diamino guanidine, i.e. with the guanidine derivative which is the basis for the production of the inventive new polyguanidines. Usually, an inner salt of acidic and basic moieties will form within the respective molecules in any case.

In a second aspect of the invention, a method for producing inventive polyguanidine derivatives according to the first aspect by polycondensation of a guanidine derivative or a salt thereof with a diamine is provided, which method is characterized in that MAG and/or DAG, or an acid addition salt thereof, is polycondensated with at least one diamine H$_2$N—R$_1$—NH$_2$ by heating.

Contrary to the state of the art, the method of the invention comprises reacting MAG or DAG with one or more diamines, preferably only one single diamine. This allows for the production of more clearly defined products than in the works mentioned above conducted by the Russian researchers, because in the course of the reaction no free hydrazine was detectable in the reaction mixtures produced according to the invention—neither chromatographically nor by wet chemistry. (Side) reactions with hydrazine, which were desirable in the state of the art mentioned, but are completely undesirable herein, could thus be effectively avoided.

Preferably, the method of the invention is conducted by heating a salt of MAG or DAG, in particular the hydrogen chloride thereof, together with the diamine, which is preferably used at a small molar excess, e.g. of 3 to 5 molar % or, for economic reasons, of 10 molar % at a maximum, in relation to (di-)aminoguanidine, in order to guarantee the complete conversion of the guanidine derivative, wherein heating is is initially carried out to a first, lower temperature, preferably approximately 80-150° C., more preferably 110-130° C., and then to a second, higher temperature, preferably 150-250° C., more preferably 160-180° C., in order to control the reaction rate and thus also the formation of gas. The reaction mixture is held at the first temperature for preferably 1 to 3 h, more preferably 2 h, and then at the second temperature for preferably 1 to 8 h, more preferably 3 to 5 h, in order to guarantee a complete reaction.

The reaction is preferably conducted at normal pressure and with the exclusion of water, which can, for example, be achieved by initially purging the reaction vessel with inert gas and equipping the reaction vessel with a drying tube. However, applying a vacuum is also possible, in particular at the end of the reaction in the course of a purification step in order to evaporate free ammonia as well as residual monomer, i.e. mainly excess diamines, as completely as possible.

After completion of the reaction, the polyguanidine derivative obtained is preferably dissolved in water, e.g. in the 3- to 10-fold amount of water. This serves, on the one hand, to separate any water-insoluble components and, on the other hand, an aqueous solution is a preferred formulation for the use of the new polymers, which means that it might—if applicable, after the addition of optional adjuvants—be usable directly as such.

Further purification options, which are less preferred at the moment, include for example evaporating the water from the aqueous solution and drying the polymers in a vacuum or salting out from the aqueous solution by the addition of acid and subsequent drying, where the pharmaceutically acceptable acids described as preferred are useful. One embodiment of salting out includes the introduction of $CO_2$ and salting out the polyguanidines as carbonates or hydrogen carbonates. If the desired polyguanidine is not to be used as a salt, but as a free base, salting out might be followed by treatment with a base, which may be provided in an aqueous or nonaqueous solution or suspension.

In a third aspect, the invention provides a polyguanidine derivative according to the first aspect of the invention or produced by a method according to the second aspect of the invention for the use in the human and veterinary medical fields for antagonizing bacterial, fungal and viral infections and their aftereffects, as a pesticide and disinfectant in the agricultural and environmental fields, generally as a disinfectant (biocide) for reducing and eliminating germs, as an antiparasitic, as a supplement for stabilizing (sterilizing) products, or as a nebulization substance in a dissolved form for cold/wet nebulization, micronization and vapor sterilization.

Below, the present invention will be described in more detail by means of non-limiting exemplary embodiments together with comparative examples. The only FIGURE, FIG. 1, summarizes the results of toxicity assays.

EXAMPLES

Examples 1 to 6 & Comparative Examples 1 and 2

Production of the Polymers

Example 1

23 mmol of 1,3-diaminoguanidinium hydrochloride and 24 mmol of 4,9-dioxadodecane-1,12-diamine were heated in a reaction vessel closed with a drying tube at 120° C. for 90 min with stirring, then the temperature was increased to 180° C. for 100 min, at the end of this reaction time under reduced pressure (50 mbar) for 45 min. After the reaction mixture had cooled off to below 80° C., 25 ml of water were added to the gelatinous reaction product. After several hours, a clear solution was obtained.

The water was evaporated from a sample of the aqueous solution obtained, and the residue obtained was dried in vacuum, which resulted in a reddish, viscous liquid. It was dissolved in 2 ml of $D_2O$ (with a deuterization degree >99,5%), and a $^1H$ nuclear resonance ($^1H$-NMR-) spectrum was obtained. The positions of methylene proton groups of the radical $R_1$ in the product distinguishable in this way are as follows:

$^1H$-NMR ($D_2O$), δ (ppm): 1.54-1.67 (m, OCH$_2$CH$_2$CH$_2$CH$_2$O), 1.80-1.95 (m, NCH$_2$CH$_2$), 3.23-3.38 ppm (m, NCH$_2$), 3.42-3.65 ppm (m, CH$_2$CH$_2$OCH$_2$CH$_2$).

This confirms the structure of the diamine component used, 4,9-dioxadodecane-1,12-diamine.

Example 2

4.6 mmol of 1,3-diaminoguanidinium hydrochloride and 4.8 mmol of 4,9-dioxadodecane-1,12-diamine were heated in a reaction vessel closed with a drying tube at 120° C. for 90 min with stirring, then the temperature was increased to 180° C. for 8 h, at the end of this reaction time under reduced pressure (50 mbar) for 45 min. After the reaction mixture had cooled off to below 80° C., 16 ml of water were added to the gelatinous reaction product. After several hours, a clear solution was obtained.

Example 3

4.6 mmol of N-aminoguanidinium hydrochloride and 4.8 mmol of 4,9-dioxadodecane-1,12-diamine were heated in a reaction vessel closed with a drying tube at 120° C. for 90 min with stirring, then the temperature was increased to 180° C. for 3.5 h, at the end of this reaction time under reduced pressure (50 mbar) for 60 min. After the reaction mixture had cooled off to below 80° C., 16 ml of water were added to the gelatinous reaction product. After several hours, a clear solution was obtained.

Example 4

1.16 mmol of 1,3-diaminoguanidinium hydrochloride and 1.21 mmol of tris(2-aminoethyl)amine were heated in a reaction vessel closed with a drying tube at 120° C. for 150 min with stirring, then the temperature was increased to 160° C. for 2.5 h, at the end of this reaction time under reduced pressure (50 mbar) for 45 min. After the reaction mixture had cooled off to below 80° C., 4 ml of water were added to the gelatinous reaction product. After several hours, a clear solution was obtained.

Example 5

8.12 mmol of 1,3-diaminoguanidinium hydrochloride and 8.47 mmol of tris(2-aminoethyl)amine were heated in a reaction vessel closed with a drying tube at 130° C. for 120 min with stirring, then the temperature was increased to 180° C. for 8 h, at the end of this reaction time under reduced pressure (50 mbar) for 90 min. After the reaction mixture had cooled off to below 80° C., 28 ml of water were added to the gelatinous reaction product. After several hours, a clear solution was obtained.

Example 6

2.32 mmol of 1,3-diaminoguanidinium hydrochloride and 2.43 mmol of 3,6-dioxaoctane-1,8-diamine were heated in a reaction vessel closed with a drying tube at 120° C. for 60 min with stirring, then the temperature was increased to 170° C. for 4 h, at the end of this reaction time under reduced pressure (50 mbar) for 60 min. After the reaction mixture had cooled off to below 80° C., 7 ml of water were added to the gelatinous reaction product. After several hours, a clear solution was obtained.

Comparative Example 1

23.2 mmol of guanidinium hydrochloride, 5.4 mmol of 3,6-dioxaoctane-1,8-diamine and 18.1 mmol of 1,6-diaminohexane were heated in a reaction vessel closed with a drying tube at 120° C. for 90 min with stirring, then the temperature was increased to 170° C. for 8 h, at the end of this reaction time under reduced pressure (50 mbar) for 90 min. After the reaction mixture had cooled off to below 80° C., 60 ml of water were added to the gelatinous reaction product. After several hours, a clear solution was obtained.

The structure of the polymer obtained corresponds to that disclosed in WO 2006/047800 A1.

Comparative Example 2

2.00 mmol of guanidinium hydrochloride, 1.70 mmol of 1,6-hexamethylene diamine and 0.3 mmol of hydrazine hydrate were heated in a reaction vessel closed with a drying tube at 160° C. for 90 min with stirring, then the temperature was increased to 180° C. for 3.5 h, at the end of this reaction time under reduced pressure (50 mbar) for 60 min. After the reaction mixture had cooled off to below 80° C., 4 ml of water were added to the gelatinous reaction product. After several hours, a clear solution was obtained.

The structure of the polymer obtained corresponds to that disclosed in WO 2011/043690 A1.

Example 7

Determination of Activity:
Antimicrobial/Antifungal/Antiviral Effects

The activities of the new compounds were tested in screening systems in multiplicate. The antibacterial and antifungal activities were tested in a MIC assay. MIC refers to "minimal inhibitory concentration" and is the lowest concentration of a substance that will inhibit the growth of microorganisms discernible with the naked eye. The MIC is determined using a so-called titer method, where the substance is diluted and then the pathogen is added.

Usually this allows for the determination of the concentration of an antibiotic that is just high enough to inhibit growth of a bacterial strain. The MIC is specified in micrograms per milliliter (μg/ml) or in % per volume, and the dilutions are generally conducted in log 2 steps. Herein, an initial concentration of 1% each was 2-fold diluted, which consequently resulted in test concentrations of 0.5%, 0.25%, 0.125%, etc. Lower values thus reflect better activity as anti-infective.

The assays were conducted according to the standards required by EUCAST (European Committee for Antimicrobial Susceptibility Testing) and according to the AFST ("Antifungal Susceptibility Testing") regulations of the European Society of Clinical Microbiology and Infectious Diseases (ESCMID).

The screening system for viruses is an infection system in which host cells are infected in vitro, and the test substance is added before or after the infection and its activity determined. All these assays were conducted according to internal standard regulations of SeaLife Pharma for drug screening, wherein analogous serial dilutions were used like in the antibacterial/antifungal assay.

The following tables 1 to 3 summarize the test results regarding the anti-infective effect of the inventive new compounds of Examples 1, 3, 4 and 5 against multiresistant bacteria and fungi as well as viruses. The data are mean values of multiple determinations.

It is obvious that the new compounds of the invention show excellent activity against Gram-positive as well as Gram-negative pathogens:

TABLE 1

| MIC assay results | MRSA | Staphylococcus epidermis | streptococcus pneumoniae | Enterococcus faecalis | Propionibacter acne | E. coli |
|---|---|---|---|---|---|---|
| Example 1 | 0.001% | 0.001% | 0.004% | 0.008% | 0.001% | 0.016% |
| Example 3 | 0.001% | 0.001% | 0.001% | 0.008% | 0.001% | 0.02% |
| Example 4 | 0.001% | 0.001% | 0.001% | 0.008% | 0.001% | 0.016% |
| Example 5 | 0.001% | 0.001% | 0.002% | 0.002% | 0.001% | 0.020% |

| MIC assay results | Klebsiella pneumoniae | Pseudominas aeruginosa | Acinetobacter baumanii | Enterobacter cloace | Salmonella enterica |
|---|---|---|---|---|---|
| Example 1 | 0.02% | 0.02% | 0.06% | 0.03% | 0.03% |
| Example 3 | 0.02% | 0.02% | 0.06% | 0.2% | 0.03% |
| Example 4 | 0.016% | 0.030% | 0.02% | 0.016% | 0.030% |
| Example 5 | 0.02% | 0.04% | 0.04% | 0.13% | 0.03% |

Also against fungi and yeasts:

TABLE 2

| MIC assay results | Candida albicans | Candida papillosis | Candida glabrata | Candida kruzei | Aspergillus terreus | Aspergillus fumigatus | Fusarium rosei | Trichophyton sp. | Alternarria alternarria | Microsporum canis | Dematiacea sp. |
|---|---|---|---|---|---|---|---|---|---|---|---|
| Example 1 | 0.008% | 0.03% | 0.02% | 0.02% | 0.02% | 0.03% | 0.03% | 0.02% | 0.02% | 0.03% | 0.02% |
| Example 3 | 0.02% | 0.02% | 0.02% | 0.02% | 0.03% | 0.03% | 0.03% | 0.02% | 0.02% | 0.02% | 0.02% |
| Example 4 | 0.008% | 0.016% | 0.016% | 0.008% | 0.125% | 0.125% | n.t. | n.t. | n.t. | n.t. | n.t. |
| Example 5 | 0.02% | 0.02% | 0.02% | 0.020% | 0.016% | 0.016% | n.t. | n.t. | n.t. | n.t. | n.t. |

As well as against viruses:

TABLE 3

| Virological assay results | Influenza A and B | Human rhinovirus | Parainfluenza virus | Herpes simplex virus |
|---|---|---|---|---|
| Example 1 | 0.008% | 0.008% | 0.008% | 0.02% |
| Example 3 | 0.02% | 0.02% | 0.02% | 0.02% |
| Example 4 | 0.04% | 0.02% | 0.04% | 0.02% |
| Example 5 | 0.04% | 0.04% | 0.04% | 0.02% |

Thus, all new compounds tested show very good to excellent activity against various pathogens—with significantly lower toxicity than the polyguanidine derivatives known from prior art, as is shown by the following toxicity assays.

Example 8

Toxicity Assays

AlamarBlue® Assays as described below were used to study 4 polymers with regard to their toxicological potential (including proliferation, cell death, cell metabolism), and the $IC_{50}$ value and the non-toxic concentration were determined with primary keratinocytes (HKER) and primary endothelial cells (HUVEC). FIG. 1 shows the toxic effect of the various polymers depending on their concentration.

AlamarBlue® Assay: 20,000 human keratinocytes (HKER) or endothelial cells (HUVEC) were plated in 96 well plates and incubated for 24 h, before different concentrations (5% to 0.005%) of the new polymers of Examples 1 and 3 as well as of the comparative substances of Comparative Examples 1 and 2 were added. After 24 hours, 10 µl AlamarBlue® were added to each well (100 µl medium), and after 3 hours of incubation, the color reaction was detected using a multiplate reader (ex: 530 nm; em: 590 nm). HKER: "human primary keratinocytes"; HUVEC: "human umbilical vein endothelial cells".

The polymers of Comparative Examples 1 and 2 show significant toxic effects against HKER as well as HUVEC at already very low concentrations, i.e. an $IC_{50}$ of approximately 0.01% or below. In comparison, the new polymers produced by the inventors of Examples 1 and 3 show toxic effects at significantly higher concentrations: for Example 1, the $IC_{50}$ for both cell types is approximately 1%, and for Example 3, it ranges between 0.05% and 0.1%. The toxicity produced by the comparative examples is reached by the polymer of Example 3 only at the 5-fold concentration, and by that of Example 1 only at the at least 100-fold concentration. The DAG derivative thus showed much better results in this assay than the MAG polymer.

Consequently, the new compounds show very good to excellent activity against various pathogens—with significantly lower toxicity than polyguanidine derivatives known from prior art.

The invention claimed is:

1. A polyguanidine derivative comprising a polycondensation product of aminoguanidine and/or 1,3-diaminoguanidine with at least one diamine and having the following formula (I) or a salt thereof:

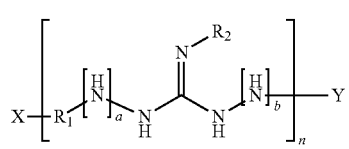

(I)

wherein
X is selected from —NH2, aminoguanidino, and 1,3-diaminoguanidino;
Y is selected from —H and —R$_1$—NH$_2$;
or X and Y together represent a chemical bond to give a cyclic structure;
R$_1$ is selected from divalent organic radicals having 2 to 20 carbon atoms, in which optionally at least one carbon atom is replaced by O or N;
a and b are each 0 or 1,
wherein a+b≠2 if no 1,3-diaminoguanidine units are contained;
R$_2$ is selected from —H and —NH2,
wherein R$_2$ is —NH$_2$ if a+b=0,
R$_2$ is —H or —NH$_2$ if a+b=1, and
R$_2$ is —H if a+b=2; and
n>2.

2. The polyguanidine derivative according to claim 1, wherein R$_1$ is selected from alkylene radicals, in which optionally at least one carbon atom is replaced by O or N.

3. The polyguanidine derivative according to claim 2, wherein R$_1$ is selected from radicals of the following general formulas (II) to (V):

 (II),

 (III),

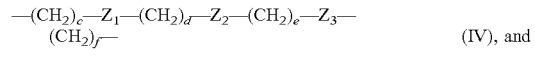 (IV), and

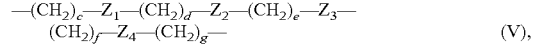 (V), wherein $Z_1$ to $Z_4$ are each independently a heteroatom selected from O and N, and indexes c to g are each independently integers in a range of 1 to 12, such that a total number of atoms of radical $R_1$ does not exceed 20.

4. The polyguanidine derivative according to claim 3, wherein all heteroatoms Z within one radical R$_1$ are either O or N.

5. The polyguanidine derivative according to claim 4, wherein R$_1$ represents a divalent radical of a polyether diamine.

6. The polyguanidine derivative according to claims 1, wherein n=2 to 6.

7. The polyguanidine derivative according to claim 1, wherein the salt is an acid addition salt in a form of a hydrogen chloride, hydrogen bromide, hydrogen iodide, sulfate, carbonate, borate, cyanate, thiocyanate, phosphate, mesylate, nitrate, acetate, benzoate, lactate, tartrate, citrate, maleate, fumarate, a partial ester of one of these acids, in case they are difunctional or higher, or as a mixture of at least two of these salts and/or partial esters.

8. A method for producing a polyguanidine derivative according to claim 1, the method comprising polycondensing a guanidine derivative selected from aminoguanidine, 1,3-diaminoguanidine and an acid addition salt thereof with at least one diamine of the formula H$_2$N—R—NH$_2$ by heating.

9. The method according to claim 8, wherein the at least one diamine is used at an excess of 3 to 5 molar % in relation to the guanidine derivative.

10. The method according to claim 8, wherein the acid addition salt of amino-guanidine or 1,3-diaminoguanidine is heated together with the at least one diamine, initially to a first, lower temperature and then to a second, higher temperature.

11. The method according to claim 10, wherein the acid addition salt of aminoguanidine or 1,3-diaminoguanidine is heated together with the at least one diamine, initially to 110-130° C. and then to 160-180° C.

12. The method according to claim 10, wherein a reaction mixture the guanidine derivative and diamine is kept at the first temperature for 1 to 3 hours and at the second temperature for 1 to 8 hours.

13. The method according to claim 8, wherein the polyguanidine derivative is purified by dissolution in approximately a 3-to 10-fold amount of water.

14. A method of using the polyguanidine derivative according to claim 1 for in human and veterinary medical fields for antagonizing bacterial, fungal and viral infections and their aftereffects.

15. A method of using the polyguanidine derivative according to claim 1 as a pesticide and disinfectant in the agricultural and environmental fields for reducing and eliminating germs.

16. A method of using the polyguanidine derivative according to claim 1 as an antiparasitic.

17. A method of using the polyguanidine derivative according to claim 1 as a supplement for stabilizing or sterilizing products.

18. A method of using the polyguanidine derivative according to claim 1 as a nebulization substance, wherein the polyguanidine derivative is present in a dissolved form for cold/wet nebulization, micronization and vapor sterilization.

19. A composition comprising the polyguanidine derivative according to claim 1, wherein an effective amount of the polyguanidine derivative is present as a solution in a 3- to 10-fold amount of water.

* * * * *